(12) United States Patent
Lucht et al.

(10) Patent No.: US 7,833,438 B2
(45) Date of Patent: *Nov. 16, 2010

(54) THERMOFLUORESCENT PIGMENTS FOR SECURITY AND SAFETY APPLICATIONS

(75) Inventors: Brett L. Lucht, Kingston, RI (US); William B. Euler, Narragansett, RI (US); Yu Wang, Kingston, RI (US); Nadia Archambault, Warwick, RI (US)

(73) Assignee: The Board of Governors for Higher Education, State of Rhode Island and Providence Plantations, Providence, RI (US)

( * ) Notice: Subject to any disclaimer, the term of this patent is extended or adjusted under 35 U.S.C. 154(b) by 1023 days.

This patent is subject to a terminal disclaimer.

(21) Appl. No.: 11/582,649

(22) Filed: Oct. 18, 2006

(65) Prior Publication Data

US 2007/0077661 A1    Apr. 5, 2007

(51) Int. Cl.
G01N 31/00    (2006.01)
G01N 33/00    (2006.01)
G01N 21/76    (2006.01)
(52) U.S. Cl. .................................. 252/408.1; 436/172
(58) Field of Classification Search .............. 252/408.1; 48/195
See application file for complete search history.

(56) References Cited

U.S. PATENT DOCUMENTS

| 4,329,986 | A | * | 5/1982 | Babb ........................... 604/5.04 |
| 4,379,986 | A | * | 4/1983 | Baxter et al. ................. 318/434 |
| 6,440,745 | B1 |  | 8/2002 | Weinberg et al. |
| 6,706,218 | B2 | * | 3/2004 | Lucht et al. ............... 252/408.1 |
| 7,517,475 | B2 | * | 4/2009 | Lucht et al. ............... 252/408.1 |
| 2002/0128451 | A1 |  | 9/2002 | Raymond et al. |
| 2002/0149003 | A1 | * | 10/2002 | Lucht et al. ............... 252/408.1 |
| 2005/0112768 | A1 |  | 5/2005 | Evans et al. |

* cited by examiner

*Primary Examiner*—Jennifer K Michener
*Assistant Examiner*—Eli S Mekhlin
(74) *Attorney, Agent, or Firm*—Gauthier & Connors LLP

(57) ABSTRACT

The invention is directed to use of polythiophenes in a method to determine the genuineness of an article which method comprises providing an article treated with a composition comprised of a polythiophene, the polythiophene having a low temperature color and a weak fluorescence and the structure of the polythiophene being designed such that when the composition is placed in a heat-exchange relationship with the article, the low temperature color will change to a high temperature color and the weak fluorescence will change to a strong fluorescence when a pre-determined temperature is met or exceeded in the article, heating the article to a temperature that meets or exceeds the pre-determined temperature and detecting the color and the fluorescence change.

19 Claims, 5 Drawing Sheets

US 7,833,438 B2

THERMOFLUORESCENT PIGMENTS FOR SECURITY AND SAFETY APPLICATIONS

PRIORITY INFORMATION

This application claims the benefit of International Patent Application Serial No. PCT/US05/013013 filed on Apr. 19, 2005 and claims priority to U.S. Provisional Patent Application 60/563,515 filed on Apr. 19, 2004, all of which are incorporated herein by reference in their entirety.

BACKGROUND OF THE INVENTION

The unauthorized replication of genuine documents, e.g., currency, paid admission tickets, visas, etc., is a widespread problem. Currently, manufacturers of genuine documents incorporate markers, e.g., inks, into the documents that function to identify the documents. Thus, the genuineness of the documents is confirmed by the presence of the inks therein. However, markers exist that are comparable to the markers used by the manufacturers that can be used to produce counterfeit documents of the genuine documents thereby compromising the ability of the marker used by the manufacturers to serve its function as a genuineness indicator.

SUMMARY OF THE INVENTION

It has been unexpectedly discovered that the compounds disclosed in PCT/US02/00797 entitled "Thermochromic Polymers for Rapid Visual Assessment", filed Jan. 10, 2002, which application is hereby incorporated by reference in its entirety into the present application, reversibly exhibit a fluorescence change that is temperature dependent and that the compounds disclosed in PCT/US03/020537 entitled "Thermochromic Indicator Materials with Controlled Reversibility", filed Jun. 30, 2003, which application is hereby incorporated by reference in its entirety into the present application, reversibly or irreversibly exhibit a fluorescent change that is temperature dependent. Broadly, the invention is directed to the use of the aforementioned polythiophene compounds in method to determine the genuineness of an article.

In one aspect of the invention, polythiophenes that exhibit a reversible visually detectable color change at a proscribed temperature within the range of between about –40 to 180° C. and unexpectedly exhibit an uncontrolled detectable fluorescence change are used to the determine the genuineness of an article. The visual detection of the color change can include visual observation by an individual or detection of the exhibited color change by a sensor, which sensor would output a signal to be detected in any suitable manner. The detection of the fluorescence change can include the use of an Ocean Optics S2000 instrument having a cylindrical fiber optic reflection probe containing one source fiber and seven collection fibers. The temperature of the color change (hereinafter referred to as the thermochromic transition) can be adjusted by synthetically modifying the thermochromic polymers. It was unexpectedly discovered that the temperature of the fluorescence change (hereinafter referred to as the thermofluorescent transition) coincides with the thermochromic transition of the polythiophenes. The synthesis of polythiophenes is known in the art.

In one aspect, the invention is directed to a method of determining the genuineness of an article which comprises providing an article treated with a composition comprised of a compound having the following structure:

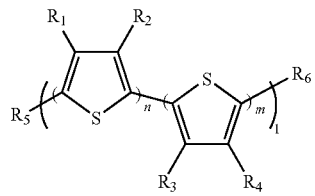

wherein $R_1$-$R_6$=a hydrogen, substituted or unsubstituted alkyl radical, substituted or unsubstituted alkoxy radical, substituted or unsubstituted aryl radical, substituted or unsubstituted thioalkyl radical, substituted or unsubstituted trialkylsilyl radical, substituted or unsubstituted acyl radical, substituted or unsubstituted ester radical, substituted or unsubstituted amine radical, substituted or unsubstituted amide radical, substituted or unsubstituted heteroaryl or substituted or unsubstituted aryl radical n is between 1 and 1000,
m is between 0 and 1000,
l is between 1 and 1000; and a carrier medium, the compound having a low temperature color and having a weak fluorescence and the structure of the compound being designed such that when the composition is placed in a heat-exchange relationship with the article, the low temperature color will change to a high temperature color and the weak fluorescence will change to a strong fluorescence when the a pre-determined temperature is met or exceeded in the article, heating the article to a temperature that meets or exceeds the pre-determined temperature and detecting the color and fluorescence change.

In yet another aspect, the invention is directed to a method of determining the genuineness of an article which comprises providing an article treated with a compound having the following structure:

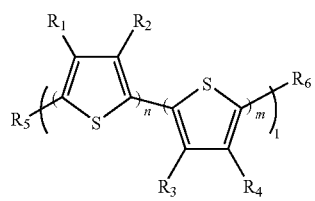

wherein $R_1$-$R_6$=a hydrogen, substituted or unsubstituted alkyl radical, substituted or unsubstituted alkoxy radical, substituted or unsubstituted aryl radical, substituted or unsubstituted thioalkyl radical, substituted or unsubstituted trialkylsilyl radical, substituted or unsubstituted acyl radical, substituted or unsubstituted ester radical, substituted or unsubstituted amine radical, substituted or unsubstituted amide radical, substituted or unsubstituted heteroaryl or substituted or unsubstituted aryl radical n is between 1 and 1000,
m is between 0 and 1000,
is between 1 and 1000; and the compound having a low temperature color and having a weak fluorescence and the structure of the compound being designed such that when the composition is placed in a heat-exchange relationship with the article, the low temperature color will change to a high temperature color and the weak fluorescence will change to a strong fluorescence when the pre-determined temperature is met or exceeded in the article, heating the article to a temperature that meets or exceeds the pre-determined temperature and detecting the color and fluorescence change.

As used herein, weak fluorescence of a compound is defined as exhibiting no visually detectable fluorescence upon irradiation with light having a wavelength within the range of between about 250-550 nm, preferably 365 nm, and strong fluorescence of a compound is defined as exhibiting visually detectable fluorescence upon irradiation with light having a wavelength within the range of between about 250-550 nm, preferably 365 nm.

In another aspect, the compound changes from the low temperature color to the high temperature color within plus or minus 5-10° C. below the pre-determined temperature.

In yet another aspect of the invention, polythiophenes that exhibit a controlled, visually detectable color change at a proscribed temperature, e.g., within the range of between about 0° C. to 150° C., preferably 40-135° C. and unexpectedly exhibit a controlled, visually detectable fluorescence change are used to detect the genuineness of an article. The visual detection of the color change can include visual observation by an individual or detection of the exhibited color change by a sensor, which sensor would output a signal to be detected in any suitable manner. The detection of the fluorescence can include irradiation of the polythiophenes with light having a wavelength within the range of between about 250-550 nm, preferably 365 nm, and visual observation by an individual or detection of the fluorescence by a sensor, which sensor would output a signal to be detected in any suitable manner, e.g., an Ocean Optics S2000 instrument having a cylindrical fiber optic reflection probe containing one source fiber and seven collection fibers.

The polythiophenes that exhibit the controlled, visually detectable color change at a proscribed temperature and exhibit a controlled, visually detectable fluorescence change are produced by subjecting the polythiophenes that exhibit a reversible visually detectable color change and unexpectedly exhibit an uncontrolled detectable fluorescence change to the conditions set forth below.

Upon heating the polythiophenes to a high temperature within the range of between about 130° C. and 160° C., preferably 140° C., the polythiophenes will change from a first low temperature color to a high temperature color. The polythiophenes are rapidly cooled to change from the high temperature color to a second low temperature color and will maintain the second low temperature color when maintained at a temperature within the range of between about 0° C. and 30° C., preferably 20° C. In addition to exhibiting the second low temperature color, the polythiophenes unexpectedly exhibited a second low temperature fluorescence. When the polythiophenes are reheated above the thermochromic transition, the polythiophenes will exhibit the high temperature color and unexpectedly exhibit a high temperature fluorescence. The polythiophenes are then allowed to cool slowly below the thermochromic transition whereupon the polythiophenes revert to the first low temperature color and unexpectedly exhibit a first low temperature fluorescence. This controlled reversible thermochromic transition results from the heating of the sample to a high temperature followed by the rapid cooling of the sample. These polythiophenes, when used as pigments to mark an item, can indicate the genuineness of the item by exhibiting expected color and fluorescence changes when exposed to temperatures known only to the manufacturer of the item. Items coated with the polythiophenes show no detectable loss of the changed color or will exhibit no detectable low of the changed fluorescence when after more than one year of storage below the thermochromic transition. The polythiophenes can be dispersed in commercial plastics (polyurethane, polystyrene, polyethylene, etc.) at low concentrations and retain the controlled reversibility. The polythiophenes can also be used as a pigment for inks.

In yet another aspect, the invention is directed to a method of determining the genuineness of an article which comprises providing a composition comprised of a compound having the following structure:

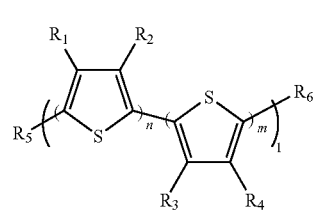

I wherein $R_1$-$R_6$=a hydrogen, substituted or unsubstituted alkyl radical, substituted or unsubstituted alkoxy radical, substituted or unsubstituted aryl radical, substituted or unsubstituted thioalkyl radical, substituted or unsubstituted trialkylsilyl radical, substituted or unsubstituted acyl radical, substituted or unsubstituted ester radical, substituted or unsubstituted amine radical, substituted or unsubstituted amide radical, substituted or unsubstituted aryl radical or substituted or unsubstituted aryl radical, n is between 1 and 1000, m is between 0 and 1000, and l is between 1 and 1000, and a carrier medium, the compound having a first low temperature color, a first low temperature fluorescence, a second low temperature color, a second low temperature fluorescence, a high temperature color and a high temperature fluorescence, the compound exhibiting a color change from the second low temperature color to the high temperature color and a fluorescence change from the second low temperature fluorescence to the high temperature fluorescence when the compound is exposed to a temperature that meets or exceeds a pre-determined temperature and exhibiting a color change from the high temperature color to a first low temperature color and a fluorescence change from the high temperature fluorescence to a first low temperature fluorescence when the compound is exposed to a decline in temperature from a temperature that meets or exceeds the predetermined temperature to a, temperature of within the range of between about 5 to 20° C. below the pre-determined temperature, the decline in temperature occurring in a time period of greater than 2.0 seconds, treating at least a portion of the article with the composition and detecting the change from the second low temperature color to the high temperature color and the change from the second low temperature fluorescence to the high temperature fluorescence or optionally the change from the high temperature color to the first low temperature color and the change from the high temperature fluorescence to the first low temperature fluorescence.

In another aspect of the invention, a method of determining the genuineness of an article which comprises providing a composition comprised of a compound having the following structure:

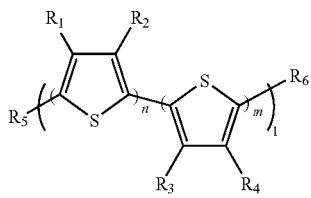

wherein $R_1$-$R_6$=a hydrogen, substituted or unsubstituted alkyl radical, substituted or unsubstituted alkoxy radical, substituted or unsubstituted aryl radical, substituted or unsubstituted thioalkyl radical, substituted or unsubstituted trialkylsilyl radical, substituted or unsubstituted acyl radical, substituted or unsubstituted ester radical, substituted or unsubstituted amine radical, substituted or unsubstituted amide radical, substituted or unsubstituted aryl radical or substituted or unsubstituted aryl radical, n is between 1 and 1000, m is between 0 and 1000, and l is between 1 and 1000; and a carrier medium, the compound having a first low temperature color, a first low temperature fluorescence, a second low temperature color, a second low temperature fluorescence, a high temperature color and a high temperature fluorescence, the compound exhibiting a color change from the second low temperature color to the high temperature color and a fluorescence change from the second low temperature fluorescence to the high temperature fluorescence when the compound is exposed to a temperature that meets or exceeds the pre-determined temperature, exhibiting a color change from the high temperature color to the first low temperature color and a fluorescence change from the high temperature fluorescence to the first low temperature fluorescence when the compound is exposed to a decline in temperature from a temperature that meets or exceeds the predetermined temperature to a temperature within the range of between about 5 to 20° C. below the pre-determined temperature that occurs in a time period greater than 2.0 seconds and exhibiting a color change from the high temperature color to the second low temperature color and a fluorescence change from the high temperature color to the second low temperature fluorescence when the compound is exposed to a decline in temperature from a temperature that meets or exceeds the predetermined temperature to a temperature of within the range of between about 20 to 50° C. below the predetermined temperature that occurs in a time period of less than 2.0 seconds, treating at least a portion of the article with the compound and detecting the change from the second low temperature color to the high temperature color and the change from the second low fluorescence to the high temperature fluorescence or optionally the change from the high temperature color to the first low temperature color and the change from the high temperature fluorescence to the low temperature fluorescence or optionally the change from the high temperature color to the second low temperature color and the change from the high temperature fluorescence to the second low temperature fluorescence.

Suitable articles can include thermopolymers, thermosetting polymers, paper, paper laminated with plastic, textiles, coated textiles, and natural and unnatural fibers. The carrier medium or composition can be generally applied to the article as a coating on an area of the article, or the entire article, which will be visible during the expected use of the article. The coating can be applied by any technique known in the art, such as by brush, roller, spraying, etc. Accordingly, the coatings typically have a thickness of 0.1 to 1000 microns. The carrier medium or composition can also be absorbed on a surface or both absorbed and adsorbed on a surface.

The carrier medium is selected from the group consisting of polyurethanes, elastomers including polysiloxanes and polydienes; polyacrylates, poly(ethylene terephthalate)s (PET), polysytrenes, polyolefins including polyethylenes (HDPE and LDPE) and polypropylene, polycarbonates, polyacrylics, polyacrylic acids, polyacrylamides, polymethacrylics, polyvinyl ethers, polyvinyl halides, poly(vinyl nitrile)s polyvinyl esters, polyesters, polysofones, polysulfonamides, polyamides, polyimines, polyimides, and carbohydrates.

As used herein, the terms low temperature color means the color the polythiophenes will exhibit below the pre-determined temperature and when the color change has either been completed or commenced. The term high temperature color means the color the polythiophenes will exhibit above the pre-determined temperature and when the color change has been either completed or commenced.

These and other objects, features and advantages of the present invention will become more apparent in light of the following detailed description of preferred embodiments thereof, as illustrated in the accompanying drawings.

BRIEF DESCRIPTION OF THE DRAWINGS

FIG. 5C depicts a polythiophene containing ink printed onto paper at room temperature under UV irradiation; and.

DETAILED DESCRIPTION OF THE INVENTION

The polythiophenes exhibiting controlled thermochromic and thermofluorescent transitions can be prepared via a two step process. Thin films or powders of polythiophenes can be heated above the thermochromic transition, typically 120-150° C., with a heat gun, oven, or hot plate. The samples are typically heated over a short period of time (5-20 seconds), but slower heating rates are appropriate also, e.g., greater than at least 20 seconds, preferably 20 to 1000 seconds. The heated films or powders are then rapidly removed from the heat, e.g., within a time period of about 0 to 10 seconds, preferably less than 2 seconds and cooled via contact with a thermally conductive material such as a metal plate. The metal plate can be at room temperature or below room temperature as long as it is at least 20° C. below the thermochromic transition temperature. The contact with the low temperature thermally conductive surface rapidly cools the polythiophenes from at or above the thermochromic transition to within 5 to 20° below the thermochromic transition within a time period less than 2 seconds, preferably 0.1 seconds, resulting in the production of the second low temperature colored material.

Polythiophenes exhibit a reversible visually detectable color change at a proscribed temperature within the range of between about −40 to 180° C. and exhibit a detectable fluorescence change are used to the determine the genuineness of an article. The visual detection of the color change can include visual observation by an individual or detection of the exhibited color change by a sensor. The temperature of the thermochromic transition can be adjusted by synthetically modifying the thermochromic polymers. It was unexpectedly discovered that the temperature of the thermofluorescent transition coincides with the thermochromic transition of the polythiophenes.

Figure 1:
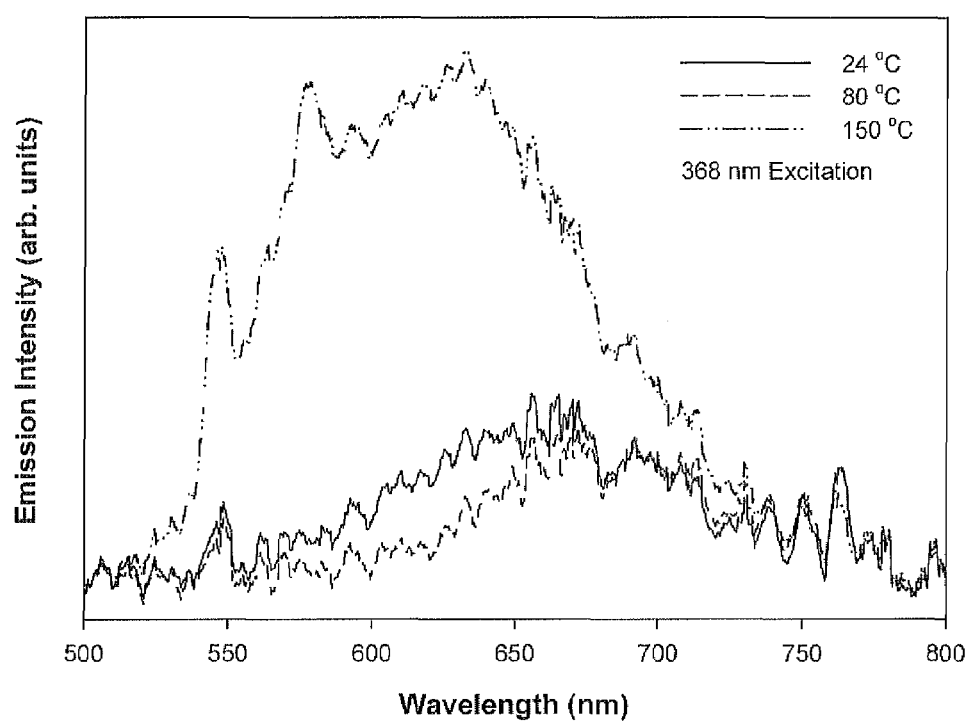
FIG. 1 is a graph showing the wavelength dependence of a thermally marked film under UV radiation which illustrates the temperature dependence fluorescence of a polythiophene film.

Referring to FIG. 1, the wavelength dependence of a thermally marked film under UV radiation which illustrates the temperature dependence fluorescence of a film comprised of a compound I wherein $R_1$ and $R_4$ are $C_{22}H_{45}$, $R_2$, $R_3$, $R_5$ and $R_6$ are H, n is 0.8, m is 0.2, and l is 40.

Figure 2:
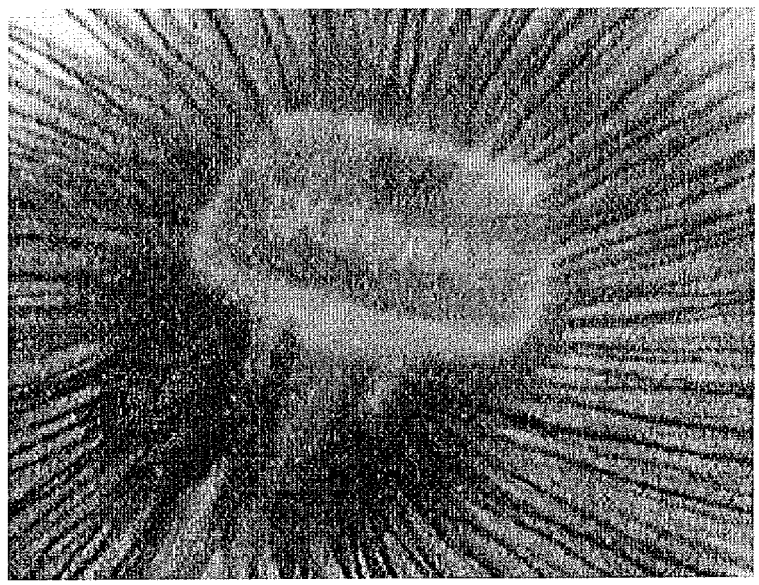
FIG. 2 depicts a film having an area marked with a polythiophene film in the shape of a key.

Referring to FIG. 2, a film is depicted having an area marked with a polythiophene film in the shape of a key. The films are comprised of compound I wherein $R_1$ and $R_4$ are $C_{22}H_{45}$, $R_2$, $R_3$, $R_5$ and $R_6$ are H, n is 0.8, m is 0.2, and l is 40.

The synthesis of the polythiophenes included oxidative polymerization of 3-docosylthiophene with $FeCl_3$ in either chloroform of methylene chloride. Thereafter the polythiophenes were coated onto a substrate by spin casting form a THF solution to form a film. At room temperature, the film, exhibiting a burgundy color was irradiated with light having a wavelength in the range of between about 250 and 550 nm by directing a the light from a UV lamp (Fisher Scientific) onto the film. The irradiated film did not exhibit a visually detectable fluorescence. To detect and measure the fluorescence, an Ocean Optics S2000 instrument using a cylindrical fiber optic reflection probe containing one source fiber and seven collection fibers the sample was used. Subsequently, the film was heated to a temperature of about 130° C. by a heat gun. The heated film exhibited a color change from burgundy to yellow and exhibited a light having a wavelength of about 525 to 650 nm when irradiated with light having a wavelength in the range of between about 250 and 550 nm by directing a light from the UV lamp. As the film in the area marked in the key cooled from 130° C. to about room temperature within a period of about 0.1 seconds (time), the color changed from yellow to light red and exhibited light having a wavelength of about 575 and 750 nm when irradiated with light having a wavelength of in the range of between about 250 and 550 nm by again directing a light from the UV lamp onto the film. The area of the film outside the key, never having been rapidly cooled, was allowed to cool from 130° C. to about room temperature, exhibited no visually detectable fluorescence upon irradiation with light having a wavelength within the range of between about 250 and 550 nm by directing the light from the UV lamp and exhibited a color change from yellow to burgundy. In addition, if the area of film in the shape of the key is again heated to a temperature between 120 and 150° C. and then allowed to cool to room temperature in greater than 2.0 seconds, the key can exhibit a color change from yellow to burgundy and can exhibit a light having a wavelength within the range of between about 625 and 750 nm when irradiated with light within the range of between about 250 and 550 nm by directing the light from the UV lamp.

Figure 3A:
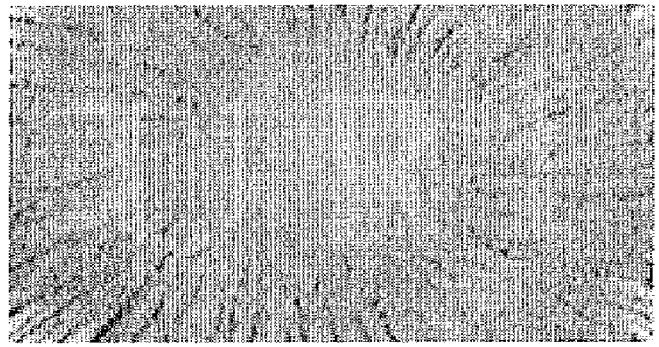
FIG. 3A depicts a film having an area marked with the letters "URI" without irradiation by UV irradiation.
Figure 3B:
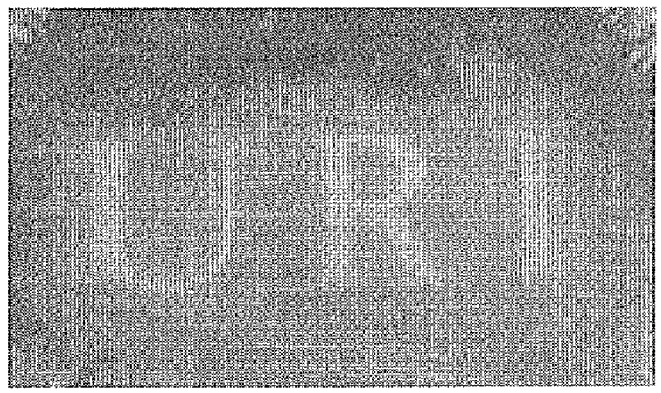
FIG. 3B depicts the film of 3A exhibiting a medium intensity low temperature fluorescence.

Referring to FIG. 3A, a film is depicted having an area marked with the letters "URI" that under natural room light, no fluorescence is observed. Referring to FIG. 3B, the film in FIG. 3A is shown exhibiting a medium intensity low temperature fluorescence upon irradiation by a UV lamp at 365 nm. The film is comprised of compound I wherein $R_1$ and $R_4$ are $C_{22}H_{45}$, $R_2$, $R_3$, $R_5$ and $R_6$ are H, n is>0.95, m is<0.05, and l is 40. These films were prepared via Grignard metathesis polymerization as reported by McCullough, R. D. and S. D. Williams, Journal of American Chemical Society, 1993, Vol. 115, pg. 11608.

The films in FIGS. 3A and 3B were spin coated from THF solutions of the polythiophene onto paper. After spin coating, the films were heated with a heat gun to between 120 and 150° C. and then were allowed to slowly cool (>2 seconds) to room temperature to remove any residual solvent. The low temperature films are purple (color) and have undetectable fluorescence emission. After heating films to between 120 and 150° C. the films can be rapidly cooled (0.1 second) by pressing a metal fuse onto the surface of the film. Rapid cooling to low temperature, 0 to 30° C., allows the generation of an red (color) mark in the form of URI, which URI will emit light having a wavelength of about 500 to 600 nm when excited with a UV lamp (345 nm) and detected either by the eye or an Ocean Optics S2000 instrument using a cylindrical fiber optic reflection probe containing one source fiber and seven collection fibers. The remainder of the film, which cooled slowly, returns to the original low temperature color, purple and the fluorescence emission is not detectable by the above mention methods. If the film is maintained at temperatures below the thermochromic transition of the polythiophene film (80° C.) the URI mark will be retained for more than a year and the mark will fluoresce at wavelength of about 500 to 600 nm when tested.

Figure 4:
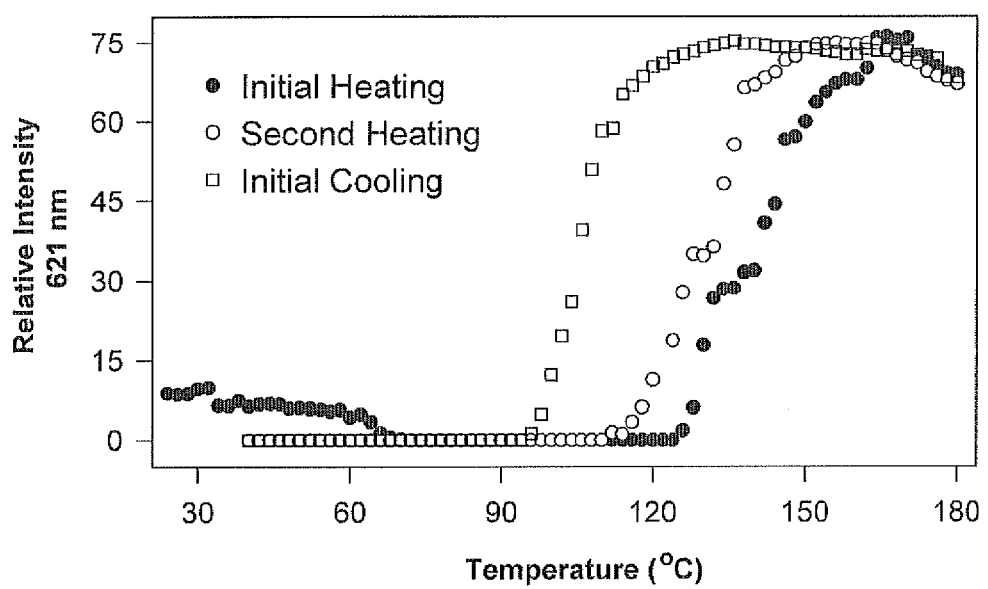
FIG. 4 is a plot showing the fluorescence intensity at 621 nm as a function of temperature demonstration the change in intensity.
Figure 5A:
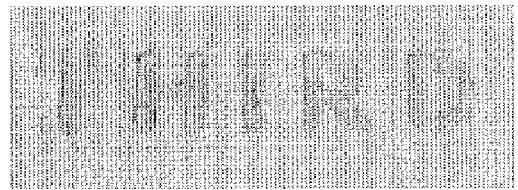
FIG. 5A depicts a polythiophene containing ink printed onto paper at room temperature under room light.
Figure 5B:
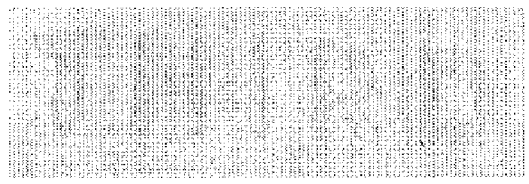
FIG. 5B depicts a polythiopene ink printed on paper heated above the thermochromic transition.
Figure 5C:
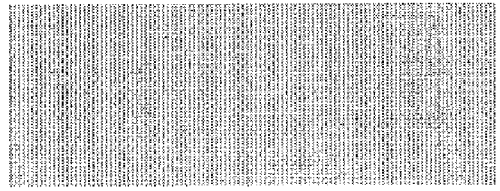
Figure 5D:
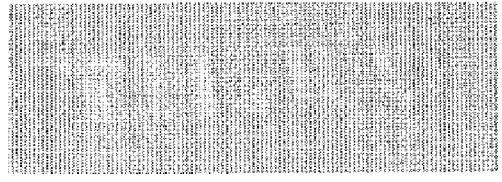
FIG. 5D depicts a polythiophene containing ink printed onto paper heated above the thermochromic transition temperature under UV irradiation.

Referring to FIG. 4, the fluorescence intensity at 621 nm of a thermally marked film under UV radiation which illustrates the temperature dependence fluorescence of a film comprised of a compound I wherein $R_1$ and $R_4$ are $C_{22}H_{45}$, $R_2$, $R_3$, $R_5$ and $R_6$ are H, n is 0.8, m is 0.2, and L is 40.

Referring to FIGS. 5A, 5B, 5C, and 5D an ink formulation composed of 5% compound I wherein $R_1$ and $R_4$ are $C_{18}H_{37}$, $R_2$, $R_3$, $R_5$, and $R_6$ are H, n is 0.80, M is 0.20, and L is 30. The synthesis of the polythiophenes included oxidative polymerization of 3-octadecylthiophene with $FeCl_3$ in either chloroform of methylene chloride. Thereafter the polythiophene was dispersed in block printing ink extender via grinding with a mortar and pestle and printed onto paper with a rubber stamp. The foregoing description has been limited to a few embodiments of the invention. It will be apparent, however, that variations and modifications can be made to the invention, with the attainment of some or all of the advantages. Therefore, it is the object of the claims to cover all such variations and modifications as come within the true spirit and scope of the invention.

What is claimed is:

1. A method of determining the genuineness of an article which comprises:

providing a composition comprised of a compound having the following structure:

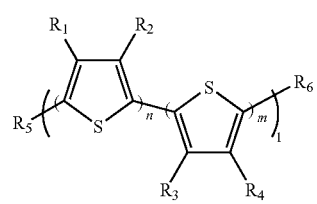

I wherein $R_1$-$R_6$=a hydrogen, substituted or unsubstituted alkyl radical, substituted or unsubstituted alkoxy radical, substituted or unsubstituted aryl radical, substituted or unsubstituted thioalkyl radical, substituted or unsubstituted trialkylsilyl radical, substituted or unsubstituted acyl radical, substituted or unsubstituted ester radical, substituted or unsubstituted amine radical, substituted or unsubstituted amide radical, substituted or unsubstituted aryl radical or substituted or unsubstituted aryl radical, n is between 1 and 1000, m is between 0 and 1000, and l is between 1 and 1000, and a carrier medium, the composition having a first low temperature color, a first low temperature fluorescence, a second low temperature color, a second low temperature fluorescence, a high temperature color and a high temperature fluorescence, the composition exhibiting a color change from the second low temperature color to the high temperature color and a fluorescence change from the second low temperature fluorescence to the high temperature fluorescence when the composition is exposed to a temperature that meets or exceeds a pre-determined temperature and exhibiting a color change from the high temperature color to a first low temperature color and a fluorescence change from the high temperature fluorescence to a first low temperature fluorescence when the composition is exposed to a decline in temperature from a temperature that meets or exceeds the predetermined temperature to a temperature of within the range of between about 5 to 20 ° C. below the pre-determined temperature, the decline in temperature occurring in a time period of greater than 2.0 seconds;

treating at least a portion of an article with the composition; and detecting the change from the second low temperature color to the high temperature color and the change from the second low fluorescence to the high temperature fluorescence or optionally detecting the change from the high temperature color to the first low temperature color and the change from the high temperature fluorescence to the low temperature fluorescence.

2. The method of claim 1 wherein the compound is present in the composition in an amount of about 0.05 to about 25.0% by weight based on the total weight of the thermal indicator material.

3. The method of claim 1 wherein $R_1$ and $R_4$ are $C_{20}$-$C_{50}$ alkyls or substituted alkyls, and $R_2$, $R_3$,$R_5$ and $R_6$ are H, n is 0.8, m is 0.2, and l is between 15 and 100, the first low temperature color is burgundy, the first low temperature fluorescence emits light having a wavelength within the range of between about 575 and 750 nm when the article is irradiated with light having a wavelength within the range of between about 250 and 550 nm, the second low temperature color is orange-red, the second low temperature fluorescence emits light having a wavelength within the range of between about 625 and 750 nm when the article is irradiated with light having a wavelength within the range of between about 250 and 550 nm, the high temperature color is yellow the high temperature fluorescence emits light having a wavelength within the range of between about 525 and 725 nm when the article is irradiated with light having a wavelength within the range of between about 250 and 550 nm, and the predetermined temperature is about 100-130° C.

4. The method of claim 1 wherein the pre-determined temperature is in the range of between about 0 to 150° C.

5. The method of claim 1 wherein $R_1$ and $R_4$ are $(CH_2)_{21}CH_3$, $R_2$, $R_3$,$R_5$ and $R_6$ are H, n is 0.8, m is 0.2, and l is between 25 and 50, the second low temperature fluores-cence emits light having a wavelength within the range of between about 625 and 750 nm when the composition is irradiated with light having a wavelength within the range of between about 250 and 550 nm, the high temperature color is yellow the high temperature fluorescence emits light having a wavelength within the range of between about 525 and 725 nm when the composition is irradiated with light having a wavelength within the range of between about 250 and 550 nm, and the predetermined temperature is about 100-130° C.

6. The method of claim 1 wherein the carrier medium is selected from the group consisting of polyurethanes; elastomers including polysiloxanes and polydienes; polyacrylates, polyethylene terephthalate)s (PET), polysytrenes, polyolefins including polyethylenes (HDPE and LDPE) and polypropylene, polycarbonates, polyacrylics, polyacrylic acids, polyacrylamides, polymethacrylics, polyvinyl ethers, polyvinyl halides, poly(vinyl nitrile)s polyvinyl esters, polyesters, polysulfones, polysulfonamides, polyamides, polyimines, polyimides, and carbohydrates.

7. The method of claim 6 wherein the carrier medium is an ink formulation.

8. The method of claim 7 wherein the ink formulation comprises oils, resins, pigment extenders and additives.

9. The method of claim 1 wherein $R_1$=$C_{22}H_{45}$, $R_2$=H, n=1, m=0, and l is between 20 to 50 or optionally wherein $R_1$=$C_{22}H_{45}$, $R_2$=H, $R_3$=H, $R_4$=$C_{22}H_{45}$, n=0.8, m=0.2, and l is between 20 to 50 or optionally wherein $R_1$=$C_{20}H_{41}$, $R_2$=H, $R_3$=H, $R_4$=$C_{20}H_{41}$, n =0.8, m=0.2, and l is between 20-50.

10. The method of claim 1 wherein the pre-determined temperature of the composition is any selected temperature within the range.

11. A method of determining the genuineness of an article which comprises:

providing a composition comprised of a compound having the following structure:

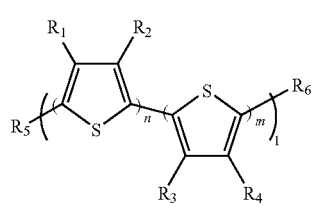

wherein $R_1$-$R_6$=a hydrogen, substituted or unsubstituted alkyl radical, substituted or unsubstituted alkoxy radical, substituted or unsubstituted aryl radical, substituted or unsubstituted thioalkyl radical, substituted or unsubstituted trialkylsilyl radical, substituted or unsubstituted acyl radical, substituted or unsubstituted ester radical, substituted or unsubstituted amine radical, substituted or unsubstituted amide radical, substituted or unsubstituted aryl radical or substituted or unsubstituted aryl radical, n is between 1 and 1000, m is between 0 and 1000, and 1 is between 1 and 1000; and a carrier medium, the composition having a first low temperature color, a first low temperature fluorescence, a second low temperature color, a second low temperature fluorescence, a high temperature color and a high temperature fluorescence, the composition exhibiting a color change from the second low temperature color to the high temperature color and a fluorescence change from the second low temperature fluorescence to the high temperature fluorescence when the compound is exposed to a temperature that meets or exceeds the predetermined temperature, exhibiting a color change from the high temperature color to the first low temperature color and a fluorescence change from the high temperature fluorescence to the first low temperature fluorescence when the compound is exposed to a decline in temperature from a temperature that meets or exceeds the predetermined temperature to a temperature within the range of between about 5 to 20° C. below the predetermined temperature that occurs in a time period greater than 2.0 seconds and exhibiting a color change from the high temperature color to the second low temperature color and a fluorescence change from the high temperature color to the second low temperature fluorescence when the compound is exposed to a decline in temperature from a temperature that meets or exceeds the predetermined temperature to a temperature of within the range of between about 20 to 50° C. below the predetermined temperature that occurs in a time period of less than 2.0 seconds;

treating at least a portion of an article with the composition; and detecting the change from the second low temperature color to the high temperature color and the change from the second low fluorescence to the high temperature fluorescence or optionally detecting the change from the high temperature color to the first low temperature color and the change from the high temperature fluorescence to the low temperature fluorescence or optionally detecting the change from the high temperature color to the second low temperature color and the change from the high temperature fluorescence to the second low temperature fluorescence.

12. The method of claim 11 wherein the compound is present in the composition in an amount of about 0.05 to about 5.0% by weight based on the total weight of the composition.

13. The method of claim 11 wherein the predetermined temperature is in the range of about 0 to 150° C.

14. The method of claim 11 wherein $R_1$ and $R_4$ are —$(CH_2)_{21}CH_3$, $R_2$, $R_3$, $R_5$ and $R_6$ are H, n is 0.8, m is 0.2, and l is between 25 and 50, the first low temperature is burgundy and the first low temperature fluorescence emits light having a wavelength within the range of between about 575 and 750 nm when the article is irradiated with light having a wavelength within the range of between about 250 and 550 nm, the second low temperature color is red-orange, the second low temperature fluorescence emits light having a wavelength within the range of between about 625 and 750 nm when the article is irradiated with light having a wavelength within the range of between about 250 and 550 nm, the high temperature color is yellow the high temperature fluorescence emits light having a wavelength within the range of between about 525 and 725 nm when the article is irradiated with light having a wavelength within the range of between about 250 and 550 nm, and the predetermined temperature is about 100-130° C.

15. The method of 11 wherein the carrier medium is selected from the group consisting of polyurethanes; elastomers including polysiloxanes and polydienes; polyacrylates, poly(ethylene terephthalate)s (PET), polysytrenes, polyolefins including polyethylenes (HDPE and LDPE) and polypropylene, polycarbonates, polyacrylics, polyacrylic acids, polyacrylamides, polymethacrylics, polyvinyl ethers, polyvinyl halides, polyvinyl nitrile)s polyvinyl esters, polyesters, polysulfones, polysulfonamides, polyamides, polyimines, polyimides, and carbohydrates.

16. The method of claim 15 wherein the carrier medium is an ink formulation.

17. The method of claim 16 wherein the ink formulation comprises oils, resins, pigment extenders and additives.

18. The method of claim 11 wherein $R_1=C_{22}H_{45}$, $R_2=H$, n=1, m=0, and l is between 20 to 50 or optionally wherein $R_1=C_{22}H_{45}$, $R_2=H$, $R_3=H$, $R_4=C_{22}H_{45}$, n=0.8, m=0.2, and l is between 20 to 50 or optionally wherein $R_1=C_{20}H_{41}$, $R_2=H$, $R_3=H$, $R_4=C_{20}H_{41}$, n=0.8, m=0.2, and l is between 20 to 50.

19. The method of claim 11 wherein the pre-determined temperature of the composition is any selected temperature within the range.

* * * * *

UNITED STATES PATENT AND TRADEMARK OFFICE
CERTIFICATE OF CORRECTION

| | | |
|---|---|---|
| PATENT NO. | : 7,833,438 B2 | Page 1 of 1 |
| APPLICATION NO. | : 11/582649 | |
| DATED | : November 16, 2010 | |
| INVENTOR(S) | : Lucht et al. | |

It is certified that error appears in the above-identified patent and that said Letters Patent is hereby corrected as shown below:

On the cover page, please add the following:

Related U.S. Application Data
(63) Continuation of application no. PCT/US2005/013013, filed on April 19, 2005.

(60) Provisional application no. 60/563,515, filed on April 19, 2004.

Signed and Sealed this
Fourth Day of January, 2011

David J. Kappos
*Director of the United States Patent and Trademark Office*